United States Patent [19]

Davie et al.

[11] Patent Number: 5,736,379

[45] Date of Patent: *Apr. 7, 1998

[54] DNA SEQUENCES EXPRESSING MAMMALIAN $\alpha_1$ ANTITRYPSIN

[75] Inventors: Earl W. Davie, Bellevue; Kotoku Kurachi, Seattle, both of Wash.; Savio L. C. Woo; Chandra Thirumalachary, both of Houston, Tex.

[73] Assignee: Washington Research Foundation, Seattle, Wash.

[ * ] Notice: The term of this patent shall not extend beyond the expiration date of Pat. No. 5,399,684.

[21] Appl. No.: 479,545

[22] Filed: Jun. 7, 1995

Related U.S. Application Data

[63] Continuation of Ser. No. 361,689, Dec. 12, 1994, abandoned, which is a continuation of Ser. No. 86,442, Jul. 2, 1993, Pat. No. 5,399,684, which is a continuation of Ser. No. 979,556, Nov. 18, 1992, abandoned, which is a continuation of Ser. No. 666,450, Mar. 11, 1991, abandoned, which is a continuation of Ser. No. 398,288, Aug. 22, 1989, abandoned, which is a continuation of Ser. No. 246,912, Sep. 16, 1988, abandoned, which is a continuation of Ser. No. 133,190, Dec. 15, 1987, abandoned, which is a continuation of Ser. No. 22,543, Mar. 3, 1987, abandoned, which is a continuation of Ser. No. 638,980, Feb. 7, 1984, abandoned, which is a continuation of Ser. No. 380,310, May 20, 1982, abandoned.

[51] Int. Cl.⁶ .......................... C12N 15/00; C12N 15/12
[52] U.S. Cl. .......................... 435/252.3; 435/320.1; 530/23.5

[58] Field of Search .................. 435/69.2, 91.1, 435/172.1, 172.3, 252.3–252.35, 325, 320.1; 536/23.5; 530/380; 935/11, 14, 29, 34, 66–75

[56] References Cited

U.S. PATENT DOCUMENTS

| 4,530,901 | 7/1985 | Weissmann | 435/172.3 |
| 5,399,684 | 3/1995 | Davie et al. | 536/23.5 |

OTHER PUBLICATIONS

Woo et al, 25th Annual Meeting of Am. Soc. for Cell Biol., J. Cell biol. 91: abstract 7061 (1981).
Davie et al, Protein, Nucleic Acid and Enzyme 27: 1805 (1981).
Kurache et al, Fed. Proc., 66th Ann. Meeting, Apr. 15–23, 1982, abstract 1446.
Kurachi et al, Proc. Natl. Acad. Sci. USA 78: 6826 (1981).
Morii et al, J. Biochem. 83: 269 (1978).
Houghton et al, Nucleic Acids Res. 8: 1913 (1980).
Suggs et al, Proc. Natl. Acad. Sci. USA 78: 6613 (1981).

Primary Examiner—James Martinell
Attorney, Agent, or Firm—Christensen O'Connor Johnson & Kindness PLLC

[57] ABSTRACT

DNA sequences to mammalian $\alpha_1$-antitrypsin are provided which can be used for expression of mammalian $\alpha_1$-antitrypsin.

This work was supported in part by grants HL16919 and HL27509 from the National Institutes of Health.

5 Claims, 11 Drawing Sheets

```
5'  G G G G G G G G G G G G G A G T G A A T C G A C A
-24                                  -20
    Met Pro Ser Ser Val Ser Trp Gly Ile Leu
    A T G C C G T C T T C T G T C T C G T G G G G C A T C C T C
+1                      10                      20                      30

Leu Leu Ala Gly Leu Cys Cys Leu Val Pro
    C T G C T G G C A G G C C T G T G C T G C C T G G T C C C T
                    40          -10             50                      60

Val Ser Leu Ala Glu Asp Pro Gln Gly Asp
    G T C T C C C T G G C T G A G G A T C C C C A G G G A G A T
                    70  -1  1                   80                      90
                                    10

Ala Ala Gln Lys Thr Asp Thr Ser His His
    G C T G C C C A G A A G A C A G A T A C A T C C C A C C A T
                    100                     110                     120
```

FIGURE 1A

```
              20                                              
Asp Gln Asp His Pro Thr Phe Asn Lys Ile
GATCAGGATCACCCAACCTTCAACAAGATC
              130             140             150

30
Thr Pro Asn Leu Ala Glu Phe Ala Phe Ser
ACCCCAAACTTGGCTGAGTTCGCCTTCAGC
              160             170             180

40
Leu Tyr Arg Gln Leu Ala His Gln Ser Asn
CTATACCGCCAGCTGGCACACCAGTCCAAC
              190             200             210

50
Ser Thr Asn Ile Phe Phe Ser Pro Val Ser
AGCACCAATATCTTCTTCTCCCCAGTGAGC
              220             230             240
```

FIGURE 1B

```
      60                                          70
Ile Ala Thr Ala Phe Ala Met Leu Ser Leu      Gly Thr Lys Ala Asp Thr His Asp Glu Ile
ATC GCT ACA GCC TTT GCA ATG CTC TCC CTG      GGG ACC AAG GCT GAC ACT CAC GAT GAA ATC
            250               260      270              280               290      300

80                                          90
Leu Glu Gly Leu Asn Phe Asn Leu Thr Glu      Ile Pro Glu Ala Gln Ile His Glu Gly Phe
CTG GAG GGC CTG AAT TTC AAC CTT CAC GGA G    ATT CCG GAG GCT CAG ATC CAT GAA GGC TTC
            310               320      330              340               350      360
```

FIGURE 1C

```
        100
Gln Glu Leu Leu Arg Thr Leu Asn Gln Pro
CAG GAA CTC CTC CGT ACC CTC AAC CAG CCA
            370              380       390

110
Asp Ser Gln Leu Gln Leu Thr Thr Gly Asn
GAC AGC CAG CTC CAG CTG ACC ACC GGC AAT
            400              410       420

120
Gly Leu Phe Leu Ser Glu Gly Leu Lys Leu
GGC CTG TTC CTC AGC GAG GGC CTG AAG CTA
            430              440       450

130
Val Asp Lys Phe Leu Glu Asp Val Lys Lys
GTG GAT AAG TTT TTG GAG GAT GTT AAA AAG
            460              470       480
```

FIGURE 1D

```
            140
Leu Tyr His Ser Glu Ala Phe Thr Val Asn
TTG TAC CAC TCA GAA GCC TTC ACT GTC AAC
        490             500             510
            150
Phe Gly Asp Thr Glu Glu Ala Lys Lys Gln
TTC GGG GAC ACC GAA GAG GCC AAG AAA CAG
        520             530             540
            160
Ile Asn Asp Tyr Val Glu Lys Gly Thr Gln
ATC AAC GAT TAC GTG GAG AAG GGT ACT CAA
        550             560             570
            170
Gly Lys Ile Val Asp Leu Val Lys Glu Leu
GGG AAA ATT GTG GAT TTG GTC AAG GAG CTT
        580             590             600
```

FIGURE 1E

```
                180
Asp Arg Asp Thr Val Phe Ala Leu Val Asn
GAC AGA GAC ACA GTT TTT GCT CTG GTG AAT
        610             620             630

190
Tyr Ile Phe Phe Lys Gly Lys Trp Glu Arg
TAC ATC TTC TTT AAA GGC AAA TGG GAG AGA
        640             650             660

200
Pro Phe Glu Val Lys Asp Thr Glu Glu Glu
CCC TTT GAA GTC AAG GAC ACC GAG GAA GAG
        670             680             690

210
Asp Phe His Val Asp Gln Val Thr Thr Val
GAC TTC CAC GTG GAC CAG GTG ACC ACC GTG
        700             710             720
```

FIGURE 1F

```
          220                    
Lys Val Pro Met Met Lys Arg Leu Gly Met
AAG GTG CCT ATG ATG AAG CGT TTA GGC ATG
        730             740         750

230
Phe Asn Ile Gln His Cys Lys Lys Leu Ser
TTT AAC ATC CAG CAC TGT AAG AAG CTG TCC
        760             770         780

240
Ser Trp Val Leu Leu Met Lys Tyr Leu Gly
AGC TGG GTG CTG CTG ATG AAA TAC CTG GGC
        790             800         810

250
Asn Ala Thr Ala Ile Phe Phe Leu Pro Asp
AAT GCC ACC GCC ATC TTC TTC CTG CCT GAT
        820             830         840
```

FIGURE 1G

```
                                             260
Glu  Gly  Lys  Leu  Gln  His  Leu  Glu  Asn  Glu
GAG  GGG  AAA  CTA  CAG  CAC  CTG  GAA  AAT  GAA
         850                 860                870

270
Leu  Thr  His  Asp  Ile  Ile  Thr  Lys  Phe  Leu
CTC  ACC  CAC  GAT  ATC  ATC  ACC  AAG  TTC  CTG
         880                 890                900

280
Glu  Asn  Glu  Asp  Arg  Arg  Ser  Ala  Ser  Leu
GAA  AAT  GAA  GAC  AGA  AGG  TCT  GCC  AGC  TTA
         910                 920                930

290
His  Leu  Pro  Lys  Leu  Ser  Ile  Thr  Gly  Thr
CAT  TTA  CCC  AAA  CTG  TCC  ATT  ACT  GGA  ACC
         940                 950                960
```

FIGURE 1H

```
                                    300
        Tyr Asp Leu Lys Ser Val Leu Gly Gln Leu
        T A T G A T C T G A A G A G C G T C C T A G G T C A A C T G
                970         980         990

310
        Gly Ile Thr Lys Val Phe Ser Asn Gly Ala
        G G C A T C A C T A A G G T C T T C A G C A A T G G G G C T
                1000        1010        1020

320
        Asp Leu Ser Gly Val Thr Glu Glu Ala Pro
        G A C C T C T C C G G G G T C A C A G A G G A G G C A C C C
                1030        1040        1050

330
        Leu Lys Leu Ser Lys Ala Val His Lys Ala
        C T G A A G C T C T C C A A G G C C G T G C A T A A G G C T
                1060        1070        1080
```

FIGURE 1I

```
                340
Val Leu Thr Ile Asp Glu Lys Gly Thr Glu
GTG CTG ACC ATC GAC GAG AAA GGG ACT GAA
            1090          1100         1110

350
Ala Ala Gly Ala Met Phe Leu Glu Ala Ile
GCT GCT GGG GCC ATG TTT TTA GAG GCC ATA
            1120          1130         1140

360
Pro Met Ser Ile Arg Pro Glu Val Lys Phe
CCC ATG TCT ATC CGC CCC GAG GTC AAG TTC
            1150          1160         1170

370
Asn Lys Pro Phe Val Phe Leu Met Ile Glu
AAC AAA CCC TTT GTC TTC TTA ATG ATT GAA
            1180          1190         1200
```

FIGURE 1J

```
        380                     Lys Ser Pro Leu Phe Met Gly
Gln Asn Thr Lys Ser Pro Leu Phe Met Gly
CAA AAT ACC AAG TCT CCC CTC TTC ATG GGA
                1210            1220            1230

390                     394
Lys Val Val Asn Pro Thr Gln Lys STOP
AAA GTG GTG AAT CCC ACC CAA AAA TAA CTG
                1240            1250
CCT CTC GCT CCT CAA CCC CCC CCC C  3'
```

FIGURE 1K

DNA SEQUENCES EXPRESSING MAMMALIAN $\alpha_1$ ANTITRYPSIN

This application is a continuation application based on prior copending application Ser. No. 08/361,689, filed on Dec. 12, 1994, now abandoned, which is a continuation of the prior application Ser. No. 08/086,442, filed Jul. 2, 1993 (U.S. Pat. No. 5,399,684), which is a continuation of application Ser. No. 07/979,556, filed Nov. 18, 1992, now abandoned, which is a continuation of application Ser. No. 07/666,450 filed on Mar. 11, 1991, now abandoned, which is a continuation of application Ser. No. 07/398,288 filed on Aug. 22, 1989, now abandoned, which is a continuation of application Ser. No. 07/246,912 filed on Sep. 16, 1988, now abandoned, which is a continuation of application Ser. No. 07/133,190 filed on Dec. 15, 1987, now abandoned, which is a continuation of application Ser. No. 07/022,543 filed on Mar. 3, 1987, now abandoned, which is a continuation of application Ser. No. 06/638,980 filed on Feb. 7, 1984, now abandoned, which is a continuation of application Ser. No. 06/380,310 filed on May 20, 1982, now abandoned, the benefit of the filing dates of which are hereby claimed under 35 U.S.C. § 120.

BACKGROUND OF THE INVENTION

1. Field of the Invention $\alpha_1$-Antitrypsin is an important protease inhibitor present in mammalian blood. Its major physiological function appears to be the inhibition of neturophil elastase, a potent protease that hydrolyzes structural proteins. It also inhibits many other serine proteases.

A low level of $\alpha_1$-antitrypsin in the blood is often associated with chronic obstructive pulmonary emphysema and infantile liver cirrhosis. At present, more than 30 different genetic variants have been identified. Several of these are associated with low concentrations of the inhibitor in the blood.

The normal plasma level of $\alpha_1$-antitrypsin is about 2 mg/ml. Under most inflammatory conditions, an acute-phase response is initiated and the concentration of $\alpha_1$-antitrypsin is subtantially increased. In order to study $\alpha_1$-antitrypsin deficiency at the molecular level and examine the mechanism of the acute phase response, it would be desirable to have pure $\alpha_1$-antitrypsin polypeptide. The $\alpha_1$-antitrypsin polypeptide could be used for the formation of antibodies to the numerous determinant sites to provide for detection of variants in the blood, as a ligand in assays for $\alpha_1$-antitrypsin, and for introduction into a host having $\alpha_1$-antitrypsin deficiency.

2. Description of the Prior Art

Shochat, et al., J. Biol. Chem. (1978), 253:5630–5634; Morii, et al., J. Biochem. (1978), 83:269–277; Carrell, et al., Biochem. Biophys. Res. Commun. (1979), 91:1032–1037; Nega, et al., J. Biol. Chem. (1980), 255:4057–4061; and Crawford, Arch. Biochem. Biophys. (1973), 156:215–222; have reported various characteristics of $\alpha_1$-antitrypsin. Kurachi, et al., PNAS (1981), 78:6826–6830, and Chandra, et al., Biochem. Biophys. Res. Comm. (1981), 103:751–758, describe cloning and sequencing of cDNA coding for $\alpha_1$-antitrypsin.

SUMMARY OF THE INVENTION

DNA sequences, including cDNA and rDNA capable of expressing mammalian $\alpha_1$-antitrypsin are provided, as well as compositions and methods for producing the polypeptide chain of $\alpha_1$-antitrypsin. $\alpha_1$-Antitrypsin polypeptide made by recombinant DNA is provided.

BRIEF DESCRIPTION OF THE DRAWINGS

FIGS. 1A–1K set forth the human $\alpha_1$-antitrypsin cDNA discussed in the specification.

DESCRIPTION OF THE SPECIFIC EMBODIMENTS

DNA sequences capable of expression of polypeptides having mammalian $\alpha_1$-antitrypsin biological activity are provided. The sequences can be used for introduction into a host cell to enhance the production of products having $\alpha_1$-antitrypsin activity. The DNA sequences include DNA sequences having exons and introns free of their normal flanking regions, messenger RNA which has been matured and is capped and includes a polyA 3' chain, cDNA obtained by transcribing mRNA and the combination of the DNA with DNA sequences, which provide regulatory signals for expression, replication, amplification, and regulated response to a variety of conditions and reagents.

The nucleic acid sequences and their expression products are polypeptides having $\alpha_1$-antitrypsin activity, in that the compounds inhibit elastase by forming an equimolar complex of the enzyme and the inhibitor with an association rate constant of greater than about $10^6$ per mole-sec. The compounds are derived from mammals, particularly primates, such as baboon and human. The chromosomal DNA fragment encoding $\alpha_1$-antitrypsin is less than about 10 kb, usually less than about 9 kb. The approximate sizes of the exon regions I, II, III, and IV are, respectively, about 0.71, 0.33, 0.13, and 0.2 kb's in length. The sizes of the introns A, B, and C are, respectively, about 1.45, 1.15, and 0.8 kb's, and the three introns are generally located within the 5' half of the DNA. The cDNA encoding $\alpha_1$-antitrypsin is about 1.182 kb's in length. The mature mRNA en coding human $\alpha_1$-antitrypsin is about 1.4 kb's in length.

The DNA sequences may be used in a variety of ways. Where chromosomal DNA is employed for transformation of host cells which are capable of recognizing the intron borders and providing for the mature mRNA, the DNA may be calcium precipitated in accordance with conventional ways and used for transformation of primate cells. For the most part, cells which can grow in vitro are cancerous and various cancerous lines may be employed for transformation. Particularly, cells of hepatic origin; e.g., hepatomas, may be employed. One may then select for transformed cells overproducing $\alpha_1$-antitrypsin.

Rather than using bare DNA, cDNA obtained by reverse transcription of mature mRNA may be inserted into a wide variety of vectors for introduction into a host for expression of $\alpha_1$-antitrypsin. The particular vector will depend upon the host and other considerations affecting the efficiency of production of the $\alpha_1$-antitrypsin. Hosts which may be employed for the production of $\alpha_1$-antitrypsin include unicellular microorganisms, such as the prokaryotes, bacteria, and eukaryotes, such as fungi, e.g., yeast, algae, protozoa, and the like. Vectors are available for cloning, expression, for amplification of genes, as well as providing for external controls, such as temperature, heavy metal ions, or the like.

Methods of introducing DNA into an organism and providing for amplification of genes encoded into such DNA may be found in PCT International Application Nos. US 81/00239 and US 81/00240. The choice of vector, regulatory signals, or other control systems will be primarily a matter relating to convenience, availability, fermentation equipment, economics, and intended use of the product. The aforementioned PCT patents provided for a generalized description of hybrid DNA technology, which technology is incorporated herein by reference.

The primate gene for $\alpha_1$-antitrypsin can be obtained by instituting hepatic local inflammation in a primate, then sacrificing the primate and isolating the liver. Polysomes are then obtained as described in the literature, and the polysomes synthesizing nascent $\alpha_1$-antitrypsin enriched by immunopreipitation. After analysis by mRNA-dependent cell-free translation employing reticulocyte, the desired cDNA would be obtained from the mRNA-enriched preparation. The cDNA is then restriction mapped and superfluous sequences removed or the cDNA is tailed, for example, a polydG-polydC tail, and then inserted into the cohesive ends of a vector. Based on the sequences, the cDNA may be modified in a variety of ways. Superfluous nucleotides, not involved in coding for $\alpha_1$-antitrypsin, may be removed by primer repair. See, for example, Goeddel, et al., Nucl. Acids Res. (1980), 8:4057–4074; Razin, et al., PNAS USA (1978), 75:4268–4270; and Wallace, et al., Science (1980), 209:1396–1400.

For primer repair, a synthetic single-stranded DNA oligomer is prepared which is complimentary to the 3'-terminus of the coding ("sense") strand of the gene encoding the $\alpha_1$-antitrypsin. The cDNA is denatured and the DNA oligomer hybridized to the coding strand. The hybrid is then treated with T4 DNA polymerase or E coli DNA polymerase large ("Klenow") fragment, so that a double strand is obtained where the coding strand has the ATG codon as the initial 3 nucleotides.

Alternatively, instead of including the leader sequence, one may use in vitro nutagenesis and prepare a synthetic DNA oligomer which replaces the Ala codon at -1 with the Met codon ATG. As the first step in this process, one would prepare a synthetic DNA oligomer, including at least the following sequence: GACTAGCTC, normally having not more than about six more nucleotides at the 5' end and at least about three nucleotides at the 3' end of the oligomer complimentary to the nucleotide of the coding strand of the $\alpha_1$-antitrypsin gene. After hybridizing the coding strand with the oligomer, the mismatched hybrid will then be treated with the same polymerase indicated above, so that the resulting double-stranded DNA would have a blunt-end terminus beginning with the nucleotides of the oligomer. In this way, the resulting dsDNA could be inserted into an expression vector, downstream from an appropriate promoter, and ribsomal start site, so that expression would be initiated at the synthetically created Met codon. As appropriate, linkers may be used to provide for cohesive ends or, alternatively, the DNA sequence may be blunt end ligated into the expression vector.

An alternative method would be to cleave the DNA fragment containing the sequence encoding for $\alpha_1$-antitrypsin intact and then, by employing an exonuclease, such as Bal 31, and by chewing back the terminal residues, one obtains a heterogeneous mixture of fragments. By timing the digestion, based on the number of nucleotides which must be removed, one can obtain fragments which will have the ATG codon in appropriate juxtaposition with a ribosomal start site, when such fragments are inserted into an expression vector. Initially, one may introduce the fragments into a cloning vector and, by employing appropriate probes, select for the clone having the desired fragments.

A preferred way is to follow the procedure of Heitzman et al., Nature (1981) 293:717–722, which disclosure is incorporated herein by reference. By restricting with BamHI, an intact fragment encoding for $\alpha_1$-antitrypsin is obtained except for the first two codons encoding Met and Glu. By ligating a linker having the nucleotides encoding the amino acids to the $\alpha_1$-antitrypsin frament, the entire $\alpha_1$-antitrypsin sequence may be inserted into an expression vector for expression.

In expressing the $\alpha_1$-antitrypsin, one may retain the leader sequence or remove the leader sequence, depending upon the host. Where a higher order host is employed and the leader peptide is retained, the host secretes the $\alpha_1$-antitrypsin with removal of the leader peptide.

Various vectors may be employed, such as plasmids, cosmids, or viruses. The expression vectors may conveniently be shuttle vectors, which allow for amplification in a prokaryote with expression in a eukaryote. Therefore, one would require replicons for both eukaryotes and prokaryotes in the vector. Secondly, one can provide for a wide variety of markers, such as cytotoxic resistance, viral immunity, prototrophy in an auxotrophic host, and the like. Conveniently, antibiotic resistance can be employed as a useful marker. Other features of the vector may include homologous sequences with the host gene to provide for integration of the $\alpha_1$ antitrypsin gene into the chromosome of the host. If desired, minichromosomes may be employed as described by Clarke and Carbon, PNAS USA (1980), 77:2173–2177; and Clarke and Carbon, Nature (1980), 287(5782):504–509.

The human $\alpha_1$-antitrypsin cDNA is set forth in the FIGS. 1A–1K.

The gene for the human $\alpha_1$-antitrypsin is of about 5 kd. The nucleotide coding for the $\alpha_1$-antitrypsin, including the f-Met codon and leader sequence, is 1254 nucleotides, which includes 72 nucleotides involved with the leader sequence, as compared with about 1400 nucleotides for the mature messenger RNA. The mature human $\alpha_1$-antitrypsin has 394 amino acids, as set forth in the prior sequence.

In order to describe the manner in which the DNA sequence for human $\alpha_1$-antitrypsin and baboon $\alpha_1$-antitrypsin were developed, the following examples are offered by way of illustration and not by way of limitation.

EXPERIMENTAL

Overlapping Genomic $\alpha_1$-Antitrypsin Clones

A total of 16 independent phage isolates were obtained when 2×10 6 plaques from the human genomic DNA library (Lawn, et al., Cell (1978), 15:1156–1174) were screened using the baboon $\alpha_1$-antitrypsin cDNA clone (Chandra, et al., Biochem. Biophys. Res. Comm. (1981), 103:751–758) as a hybridization probe. Subsequent analysis of the 16 isolates indicated that they originated from four independent clones. The four clones, labeled aAT135, aAT35, aAT80 and aAT101, were analyzed by restriction mapping and Southern hybridization using as probes an Mbo II fragment of pBaαla1 DNA, which contains the 3' terminal region of the baboon cDNA (Chandra, et al., ibid.) and an Hha I fragment of pBAαla2 DNA which is a baboon cDNA clone lacking only about 100 nucleotides at the 5' end of the mRNA (Kurachi, et al., PNAS USA (1981), 78:6826–6830). These results have established the orientation of the human $\alpha_1$-antitrypsin gene and have indicated that the entire gene may reside within a 9.6 kb Eco RI DNA fragment in the human genome.

Mosaic Structure of the Human $\alpha_1$-Antitrypsin Gene

The overall structure of the human $\alpha_1$-antitrypsin gene was established by electron microscopic examination of hybrid molecules formed between the cloned chromsomal DNA and baboon $\alpha_1$-antitrypsin mRNA. The mature mRNA consists of approximately 1400 nucleotides. DNA was denatured thermally and hybrids were formed subsequently under conditions that favored RNA/DNA hybridization but not DNA/DNA reassociation. From the electron micrographs and line drawings, it was evident that there are three intervening DNA loops (introns) of various sizes within the human $\alpha_1$-antitrypsin gene. The poly(A) tract in the mRNA was clearly visible in the hybrid molecule, thereby confirming the orientation of the gene. When aAT135 DNA was cleaved with Eco RI prior to hybrid formation with the baboon mRNA, the smallest intervening DNA loop was very close to one end of the DNA molecule. Numonic measurements of the hybrid molecules have indicated that the approximate sizes of exon regions I, II, III, and IV are 0.71, 0.33, 0.13 and 0.27 kb's in length, respectively. The sizes of introns A, B, and C are 1.45, 1.15, and 0.8 kb's, respectively, and all three introns appear to be located within the 3' half of the mRNA.

In order to characterize the human chromosomal $\alpha_1$-antitrypsin gene in greater detail, the 9.6 kb Eco RI DNA fragment was subcloned into the Eco RI site of pBR322. The resulting clone, pAT9.6, was analyzed by restriction mapping and Southern hybridization. Four exon segments were identified within the 9.6 kb Eco RI DNA fragment using a combination of enzymes that do not cut the baboon $\alpha_1$-antitrypsin cDNA insert in pBaαIa2 (Kurachi, et al. (1981), supra) These results confirmed the existence of three introns in the human $\alpha_1$-antitrypsin gene. The presence of only three introns in the peptide-coding region of the human chromodomal $\alpha_1$-antitrypsin gene was confirmed by DNA sequence analysis.

The 5' and 3' terminal sequences of the human $\alpha_1$-antitrypsin gene

Southern hybridization analysis between different portions of the baboon cDNA clone and human geonomic fragments generated by digestion of pAT9.6 revealed DNA fragments which hybridize uniquely with[2] either the 5' or the 3' end of the cDNA probe. By DNA sequencing, fragments of the human genomic DNA that code for amino acids at both the amino and carboxyl-terminal regions of human $\alpha_1$-antitrypsin were identified. The distance between these two regions is approximately 5 kb, which is in good agreement with our estimates of the size of the gene, based on the electron micrographs. The amino acid sequence at the amino-terminal region agrees for 30 of the 33 residues that have been published for human $\alpha_1$-antitrypsin (Morii et al., J. Biochem. (1978) 83:269–277). Amino acids that are different include $Lys_{10}$, $His_{20}$ and $Ile_{26}$, which were reported as Glu, Ser and Leu, respectiveoy. The DNA sequence corresponding to the amino-terminal region of the protein was confirmed by sequencing both strands of the geonimi DNAj. Furhtermore, the residues in question are identical to those determined for baboon $\alpha_1$-antitrypsin. The amino acid sequence containing 32 residues at the carboxyl end of the mature protein was also deduced from the genomic DNA sequence. This amino acid sequence is in complete agreement with that previously published for $\alpha_1$-antitrypsin (Carrell et al., Biochem. Biophys. Res. Comm. (1979) 91:1032–1037). Also, the genomic DNA sequence was identical with the corresponding nucleotide sequence of a human $\alpha_1$-antitrypsin cDNA clone.

The first ATG start codon at the 5' end of the $\alpha_1$-antitrypsin gene is located 24 amino acids upstream from the amino-terminal Glu residue in the mature protein. This region appears to code for a typical signal peptide, which is removed from the mature protein during intracellular processing prior to extracellular transport. The features of this signal peptide are similar to those seen for other signal peptides including an amino terminal methionine residue, a hydrophobic core flanked by regions of more polar residues, a small uncharged amino acid at the putative cleavage site, proline at position −5 and a length of ~ 15–30 amino acid residues. Furthermore, there appears to be a "TATA box" sequence located at position −25 to −31 of the gene, which resembles the consensus sequence, $$TATA^{TAT}_{ATA'}$$

proposed by Cordon et al. The transcription start point in eukaryotes also has a consensus sequence, PyCAPyPyPy-PyPy (A=position+1; Py represents pyrimidine.

Based on the description in Kurachi et al. (1981), supra, the baboon $\alpha_1$-antitrypsin gene can also be used for producing baboon $\alpha_1$-antitrypsin as described above in conjunction with the disclosure of Kurachi.

In accordance with the subject invention, $\alpha_1$-antitrypsin can be produced by hybrid DNA techniques. By virtue of the flexibility of hybrid DNA technology, large amounts of $\alpha_1$-antitrypsin free of sugar substituents can be obtained. Furthermore, by employing appropriate hosts, the presence of the leader peptide allows for secretion of the product into the nutrient medium for ease of isolation.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid which hybridizes to the human $\alpha_1$-antitrypsin cDNA shown in the FIGS. 1A–1K and which encodes a polypeptide exhibiting $\alpha_1$-antitrypsin activity.

2. An isolated nucleic acid according to claim 1, which comprises a 3' terminal coding sequence identical to the sequence AAT-CCC-ACC-CAA-AAA shown in FIGS. 1A–1K.

3. A vector comprising an isolated nucleic acid according to claim 1.

4. A host cell transformed with a vector according to claim 3.

5. A host cell transformed with an isolated nucleic acid according to claim 1.

* * * * *